(12) United States Patent
Beaussoubre et al.

(10) Patent No.: US 10,829,716 B2
(45) Date of Patent: Nov. 10, 2020

(54) PROCESS FOR PREPARING A PERFUMING COMPOSITION

(71) Applicant: FIRMENICH SA, Satigny (CH)

(72) Inventors: Pascal Beaussoubre, Geneva (CH); Wolfgang Fieber, Geneva (CH); Aude Daugeron-Jouault, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/611,564

(22) PCT Filed: May 8, 2018

(86) PCT No.: PCT/EP2018/061839
§ 371 (c)(1),
(2) Date: Nov. 7, 2019

(87) PCT Pub. No.: WO2018/206561
PCT Pub. Date: Nov. 15, 2018

(65) Prior Publication Data
US 2020/0095518 A1  Mar. 26, 2020

(30) Foreign Application Priority Data

May 11, 2017 (EP) ..................... 17170626

(51) Int. Cl.
*A61K 8/18* (2006.01)
*A61K 8/00* (2006.01)
*C11B 9/00* (2006.01)
*A61Q 13/00* (2006.01)

(52) U.S. Cl.
CPC ............ *C11B 9/0042* (2013.01); *A61Q 13/00* (2013.01); *C11B 9/0015* (2013.01)

(58) Field of Classification Search
CPC ....... C11B 9/0015; C11B 9/004; A61K 8/345; A61K 8/33; A61L 9/00; A61L 9/044; A61L 9/12; A61Q 13/00
USPC .................................... 512/14, 8, 1
See application file for complete search history.

(56) References Cited

U.S. PATENT DOCUMENTS 4,225,515 A * 9/1980 Weber ............... C11B 9/0042
568/444
2003/0232025 A1* 12/2003 Colwell ............... A61K 8/28
424/65

FOREIGN PATENT DOCUMENTS

DE  2307627 A1  9/1974
WO  9512379 A1  5/1995

OTHER PUBLICATIONS

International Search Report and Written Opinion for International Application No. PCT/EP2018/061839, dated Jul. 9, 2018. 15 pages.
Werle et al., "Alcohols, Polyhydric", Ullmann's Encyclopedia of Industrial Chemistry, Published Jul. 15, 2008, pp. 263-284, vol. 2.

* cited by examiner

*Primary Examiner* — Jessica Whiteley
(74) *Attorney, Agent, or Firm* — Armstrong Teasdale LLP

(57) ABSTRACT

Described herein is a process for preparing a stable perfuming composition including a perfume oil, a viscosifying agent including tricyclodecanedimethanol alcohol, and a perfumery carrier including dipropylene glycol.

14 Claims, No Drawings

PROCESS FOR PREPARING A PERFUMING COMPOSITION

CROSS-REFERENCE TO RELATED APPLICATIONS

This application is a U.S. National Phase Application of PCT/EP2018/061839, filed on May 8, 2018, which claims the benefit of priority to European Patent Application Number 17170626.0, filed May 11, 2017, the entire contents of which are hereby incorporated by reference herein.

TECHNICAL FIELD

The present invention relates to the field of perfuming compositions. More particularly, the present invention describes a process for preparing a stable perfuming composition comprising a perfume oil, a viscosifying agent comprising tricyclodecanedimethanol alcohol, and a perfumery carrier comprising dipropylene glycol.

A perfuming composition obtainable by said process as well as consumer products comprising said perfuming composition are also objects of the invention.

BACKGROUND OF THE INVENTION

Tricyclodecanedimethanol alcohol (also known as TCD alcohol DM) is a highly viscous additive used for viscous perfumed composition.

It is known that TCD alcohol DM tends to crystallize or even gel upon storage at room temperature.

Thus, when incorporated in consumer products comprising for example a solvent phase and a perfume, tricyclodecanedimethanol alcohol needs to be heated up to become transparent and more fluid.

However, upon storage, a recrystallization occurs in final consumer products leading to a difficult anticipation of the shelf life of the final product upon storage condition.

Some highly viscous oils (called "Mukhallat") are available on the market. Those compositions can comprise TCD alcohol DM, perfume and dipropylene glycol. However, it has been observed that they crystallize upon time, rendering the perfuming composition less appealing, and even unusable in some cases.

There is therefore a need to provide viscous perfumed composition that would be stable upon storage and that would exhibit good olfactive performance.

To our knowledge, no prior art deals with the prevention of crystallization of TCD alcohol DM in perfuming composition.

The composition of the invention solves this problem as it provides a process for preparing a perfuming composition comprising TCD alcohol DM that prevents the crystallization of said composition upon time.

SUMMARY OF THE INVENTION

A first object of the invention is a process for preparing a perfuming composition comprising the steps of:
(i) Heating a viscosifying agent comprising tricyclodecanedimethanol alcohol at a temperature greater than 90° C.,
(ii) Optionally, cooling down the solution obtained in step i) at a temperature greater than room temperature, preferably comprised between 30° C. and 80° C., and
(iii) Cooling down mixture obtained in step (i) or (ii) at room temperature,
wherein a perfumery carrier comprising dipropylene glycol is further added at any stage of the process, and
wherein a perfume oil comprising at least one perfuming ingredient is further added in step (ii) and/or in step (iii).

A second object of the invention is a perfuming composition obtainable by the process as defined above.

A third object is a consumer product comprising the perfuming composition.

DETAILED DESCRIPTION OF THE INVENTION

Unless stated otherwise, percentages (%) are meant to designate percent by weight of a composition.

The present invention has now determined a way to prevent the crystallisation of a composition comprising tricyclodecanedimethanol alcohol by heating tricyclodecanedimethanol alcohol at high temperatures, i.e. greater than 90° C.

A first object of the invention is therefore a process for preparing a perfuming composition comprising the steps of:
(i) Heating a viscosifying agent comprising tricyclodecanedimethanol alcohol at a temperature greater than 90° C.,
(ii) Optionally, cooling down the solution obtained in step i) at a temperature greater than room temperature, preferably comprised between 30° C. and 80° C., and
(iii) Cooling down mixture obtained in step (i) or (ii) at room temperature,
wherein a perfumery carrier comprising dipropylene glycol is further added at any stage of the process, and
wherein a perfume oil comprising at least one perfuming ingredient is further added in step (ii) and/or in step (iii).

According to an embodiment, the heating phase of tricyclodecanedimethanol alcohol is performed at a temperature greater than 100° C., preferably at a temperature comprised between 100° C. and 120° C.

According to the invention, dipropylene glycol can be added at any stage of the process.

According to a particular embodiment, dipropylene glycol is heated up with tricyclodecanedimethanol alcohol in step (i).

According to the volume of tricyclodecanedimethanol alcohol to be heated, the person skilled in the art will find a suitable time for the heating phase (step i)) to obtain a fluid solution.

Then, the resulting solution may be cooled down at a temperature greater than room temperature, comprised preferably between 30° C. and 80° C. before adding the oil phase and/or dipropylene glycol. This embodiment is particularly suitable when the composition to be prepared comprises a high amount of tricyclodecanedimethanol alcohol. Indeed, the high viscosity of this component at room temperature makes the mixing with other components very difficult.

By "room temperature" (RT), it should be understood a temperature comprised between 20 and 25° C.

According to another embodiment, the perfume oil and/or dipropylene glycol is added in step (iii), i.e. at room temperature if a stirring is possible.

In all embodiments, the person skilled in the art will be able to select a suitable temperature for the addition of the perfume oil to preserve the olfactive character and to avoid evaporation or deterioration of volatile ingredients.

At the end of the process, a viscous transparent solution is obtained.

The term transparent means that the solution in the absence of coloring or fluorescent agents have transmittance values in the visible light (500-800 nm) of 100% at a path length of 1 cm referenced against demineralized water at RT.

However, it should be understood that the composition can comprise coloring agent(s) while being transparent.

Typically, the composition has a turbidity less than 10NTU, preferably less than 5NTU, more preferably between 0.01 and 5NTU.

The composition has preferably a viscosity greater than 500 mPa·s at 20° C., more preferably between 500 and 5000 mPa·s, more preferably between 2000 and 5000 mPa·s at 20° C.

Viscosity can be measured by using the rheometer AR-2000 model of TA Instruments V5.4.0 at a shear rate of $21s^{-1}$.

The perfuming composition obtained by the process of the invention is a one-phase composition. In other words, a two-phase composition such as an emulsion is not included in this definition.

Perfume Oil

According to the invention, after heating tricyclodecanedimethanol alcohol, an oil phase comprising a perfume is added in the cooled solution, either in step (ii) or in step (iii).

According to a particular embodiment, the perfume oil is mixed with another ingredient selected from the group consisting of nutraceuticals, cosmetics, insect control agents and biocide actives.

According to a particular embodiment, the oil phase consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. Examples of such solvents are glycol/diol (such as dipropyleneglycol), diethyl phthalate, triethyl citrate, benzyl benzoate, isopropyl myristate, abalyn.

According to a particular embodiment, the perfuming composition is ethanol free. According to an embodiment, the perfume oil comprises at least one perfume raw material chosen in the group consisting aldehydes, alcohols, esters, ketones, ethers and mixtures thereof. According to a particular embodiment, the perfume oil comprises at least one perfume raw material chosen in the ingredients in table 1.

TABLE 1

| Perfume raw materials | |
|---|---|
| Chemical name | Common name |
| 3-HYDROXY-2-METHYL-4H-PYRAN-4-ONE | MALTOL |
| 2-ETHYL-3-HYDROXY-4(4H)-PYRANONE | ETHYL MALTOL |
| 4-(4-HYDROXYPHENYL)-2-BUTANONE | RASPBERRY KETONE |
| 4-HYDROXY-3-METHOXYBENZALDEHYDE | VANILLIN |
| 3-(1,3-BENZODIOXOL-5-YL)-2-METHYLPROPANAL | HELIONAL |
| 2-METHOXYPHENOL | GUAIACOL |
| BENZALDEHYDE | |
| 2-CHROMENONE | COUMARINE |
| 2-PHENYLETHANOL | |
| 4-METHOXYBENZALDEHYDE | |
| 7-METHYL-2H-1,5-BENZODIOXEPIN-3(4H)-ONE | CALONE ®* |
| INDOLE | INDOL |
| PHENYLACETALDEHYDE | |
| 2-METHOXY-4-(2-PROPEN-1-YL)PHENOL | EUGENOL |
| (2E)-2-METHYL-3-(4-METHYLPHENYL)-2-PROPEN-1-OL | JOSENOL ®* |
| ETHYL 2,3-EPOXY-3-PHENYLBUTANOATE | |
| 2,4-DIMETHYL-3-CYCLOHEXENE-1-CARBALDEHYDE | ZESTOVER |
| BENZYL PROPANOATE | |
| 2,4-DIMETHYL-4,4A,5,9B-TETRAHYDROINDENO[1,2-D][1,3]DIOXINE | MAGNOLAN |
| 4-NONANOLIDE | GAMMA NONALACTONE |
| 2,6,6-TRIMETHYL-1,3-CYCLOHEXADIENE-1-CARBALDEHYDE | SAFRANAL |
| 4-ETHYLPHENOL | |

TABLE 1-continued

Perfume raw materials

| Chemical name | Common name |
| --- | --- |
| 7-ISOPROPYL-2H,4H-1,5-BENZODIOXEPIN-3-ONE | CASCALONE ®* |
| ALLYL (CYCLOHEXYLOXY)ACETATE | CYCLOGALBANATE |
| 3-(4-TERT-BUTYLPHENYL)PROPANAL | BOURGEONAL |
| METHYL (2E)-2-METHYL-2-HEXENOATE | |
| METHYL 2-((1RS,2RS)-3-OXO-2-PENTYLCYCLOPENTYL)ACETATE | HEDIONE ® |
| 3,7-DIMETHYL-1,6-OCTADIEN-3-OL | LINALOL |
| (R)-3,7-DIMETHYL-6-OCTENENITRILE | |
| 1,3-NONANEDIYL DIACETATE + TETRAHYDRO-3-PENTYL-4(2H)-PYRANYL ACETATE | JASMAL |
| 2,6-DIMETHYL-5-HEPTENAL | MELONAL |
| CYCLHEXYLIDENE(PHENYL)ACETONITRILE | PEONILE ®** |
| 5-HEPTYLDIHYDRO-2(3H)-FURANONE | GAMMA UNDECALACTONE |
| (2E)-1-(2,6,6-TRIMETHYL-1,3-CYCLOHEXADIEN-1-YL)-2-BUTEN-1-ONE | DAMASCENONE |
| 3,7-DIMETHYL-6-OCTEN-1-OL | CITRONELLOL |
| 2,3,3-TRIMETHYL-1-INDANONE | SAFRALEINE ™** |
| 4-METHYL-2-(2-METHYL1-PROPEN-1-YL)TETRAHYDRO-2H-PYRAN | ROSE OXIDE |
| METHYL 2-NONYNOATE | |
| 3-(3-ISOPROPYL-1-PHENYL)BUTANAL | FLORHYDRAL ™** |
| 3,7-DIMETHYL-1,6-NONADIEN-3-OL | ETHYL LINALOL |
| 3-(4-ISOPROPYLPHENYL)-2-METHYLPROPANAL | |
| ALLYL HEXANOATE | |
| (2E)-1-(2,6,6-TRIMETHYL-1-CYCLOHEXEN-1-YL)-2-BUTEN-1-ONE | DORINONE BETA |
| (2E)-1-(2,6,6-TRIMETHYL-2-CYCLOHEXEN-1-YL)-2-BUTEN-1-ONE | DAMASCONE ALPHA |
| 1,2,3,5,6,7-HEXAHYDRO-1,1,2,3,3-PENTAMETHYL-4-INDENONE | CASHMERAN ®*** |
| (A) + (+−)-3,5,6,6-TETRAMETHYL-4-METHYLIDENE-2-HEPTANONE (B) + (+−)-(4E)-3,4,5,6,6-PENTAMETHYL-4-HEPTEN-2-ONE (C) + (+−)-(3Z)-3,4,5,6,6-PENTAMETHYL-3-HEPTEN-2-ONE (D) + (+−)-(3E)-3,4,5,6,6-PENTAMETHYL-3-HEPTEN-2-ONE (E) | KOAVONE ®*** |
| 1-ETHOXY-4-(1-ETHOXYVINYL)-3,3,5,5-TETRAMETHYLCYCLOHEXENE (A) + 4-(1-ETHOXYVINYL)-3,3,5,5-TETRAMETHYLCYCLOHEXANONE (B) | KEPHALIS |
| 2-ETHOXYNAPHTHALENE | |
| PERHYDRO-4ALPHA,8ABETA-DIMETHYL-4A-NAPHTHALENOL | |
| 4-CYCLOHEXYL-2-METHYL-2-BUTANOL | CORANOL |
| 10-UNDECENAL | |
| (E)-TRANS-ALPHA-IRONE + (E)-CIS-ALPHA-IRONE + (E)-BETA-IRONE | IRONE ALPHA |
| 8-SEC-BUTYLQUINOLINE + 6-SEC-BUTYLQUINOLINE | ISOBUTYLQUINOLEINE |
| 3-(4-METHYL-3-PENTEN-1-YL)-3-CYCLOHEXENE-1-CARBALDEHYDE + 4-(4-METHYL-3-PENTEN-1-YL)-3-CYCLOHEXENE-1-CARBALDEHYDE | |
| TRICYCLO[5.2.1.0(2,6)]DEC-3-EN-8-YL PROPANOATE + TRICYCLO[5.2.1.0(2,6)]DEC-4-EN-8-YL PROPANOATE | |
| 2-(2-METHYL-2-PROPANYL)CYCLOHEXYL ACETATE | VERDOX ™*** |
| 1,4-DIOXACYCLOHEPTADECANE-5,17-DIONE | ASTROTONE |
| ALLYL 3-CYCLOHEXYLPROPANOATE | |
| 3-METHYL-5-(2,2,3-TRIMETHYL-3-CYCLOPENTEN-1-YL)-2-PENTANOL | SANDALORP ®** |
| {1-METHYL-2-[(1,2,2-TRIMETHYLBICYCLO[3.1.0]HEX-3-YL)METHYL]CYCLOPROPYL}METHANOL | JAVANOL ®** |
| (3E)-3-METHYL-4-(2,6,6-TRIMETHYL-2-CYCLOHEXEN-1-YL)-3-BUTEN-2-ONE + (1E)-1-(2,6,6-TRIMETHYL-2-CYCLOHEXEN-1-YL)-1-PENTEN-3-ONE | ISORALDEINE |
| (4Z,8E)-1,5,8-TRIMETHYL-13-OXABICYCLO[10.1.0]TRIDECA-4,8-DIENE + (4Z,8E)-1,4,8-TRIMETHYL-13-OXABICYCLO[10.1.0]TRIDECA-4,8-DIENE | CEDROXYDE |
| 1-METHYL-4-(4-METHYL-3-PENTENYL)-3-CYCLOHEXENE-1-CARBALDEHYDE | PRECYCLEMONE B |
| 1-(2,3,8,8-TETRAMETHYL-1,2,3,4,5,6,7,8-OCTAHYDRO-2-NAPHTHALENYL)ETHANONE + 1-(2,3,8,8-TETRAMETHYL-1,2,3,4,6,7,8,8A-OCTAHYDRO-2-NAPHTHALENYL)ETHANONE + 1-(2,3,8,8-TETRAMETHYL-1,2,3,5,6,7,8,8A-OCTAHYDRO-2-NAPHTHALENYL)ETHANONE | ISO E SUPER ®*** |
| METHYL N-(7-HYDROXY-3,7-DIMETHYL-1-OCTENYL)ANTHRANILATE | ANTHRANILOL |
| 1-(3,5,5,6,8,8-HEXAMETHYL-5,6,7,8-TETRAHYDRO-2-NAPHTHALENYL)ETHANONE | TONALIDE |
| 1-[(RS,6SR)-2,2,6-TRIMETHYLCYCLOHEXYL]-3-HEXANOL | NORLIMBANOL ®* |
| 1-(6-TERT-BUTYL-1,1-DIMETHYL-4-INDANYL)-1-ETHANONE | MUSK DTI |
| 1-(2,3,8,8-TETRAMETHYL-1,2,3,4,5,6,7,8-OCTAHYDRO-2-NAPHTHALENYL)ETHANONE + 1-(2,3,8,8-TETRAMETHYL-1,2,3,4,6,7,8,8A-OCTAHYDRO-2-NAPHTHALENYL)ETHANONE + 1-(2,3,8,8-TETRAMETHYL-1,2,3,5,6,7,8,8A-OCTAHYDRO-2-NAPHTHALENYL)ETHANONE | DERAMBRENE |
| CEDRAN-8-YL ACETATE | |
| (3ARS,5ASR,9ASR,9BRS)-3A,6,6,9A-TETRAMETHYLDODECAHYDRONAPHTHO[2,1-B]FURAN | CETALOX ®* |
| 1-(2,2,3,6-TETRAMETHYL-CYCLOHEXYL)-3-HEXANOL | LIMBANOL ®* |
| (4E)-3-METHYL-4-CYCLOPENTADECEN-1-ONE + (5E)-3-METHYL-5-CYCLOPENTADECEN-1-ONE + -(5Z)-3-METHYL-5-CYCLOPENTADECEN-1-ONE | MUSCENONE ® DELTA |
| (3AR,5AS,9AS,9BR)-3A,6,6,9A-TETRAMETHYLDODECAHYDRONAPHTHO[2,1-B]FURAN | AMBROX ®* |
| (3ARS,5ASR,9ASR,9BSR)-3A,6,6,9A-TETRAMETHYLDODECAHYDRONAPHTHO(2,1-B)FURAN | CACHALOX ®* |
| 8-METHOXYCEDRANE | CEDRAMBER |

TABLE 1-continued

Perfume raw materials

| Chemical name | Common name |
|---|---|
| 2/3/4-(5,5,6-TRIMETHYLBICYCLO[2.2.1]HEPT-2-YL)-1-CYCLOHEXANOL + 2-(1,7,7-TRIMETHYLBICYCLO[2.2.1]HEPT-2-YL)-1-CYCLOHEXANOL | SANDELA ®** |
| CEDRAN-8-YL ACETATE | |

*Origin: Firmenich SA, Geneva, Switzerland
**Origin: Givaudan SA, Vernier, Suisse
***Origin: International Flavors & Fragrances, USA According to an embodiment, up to 50% by weight of perfume oil based on the total weight of the composition is added in step (ii) or in step (iii).

Preferably from 3% to 50%, more preferably from 10% to 30%, even more preferably from 15% to 20% by weight of perfume oil based on the total weight of the composition is added in step (ii) or (iii) of the process.

Viscosifying Agent

According to a particular embodiment, the viscosifying agent consists of tricyclodecanedimethanol alcohol.

TCD alcohol DM heated up in step (i) of the process represents from 5% to 60%, preferably from 35% to 60%, more preferably from 50% to 60% by weight of the final composition.

Tricyclodecanedimethanol alcohol (TCD alcohol DM) is commercially available from OXEA GmbH.

Perfumery Carrier

According to the invention, a perfumery carrier comprising dipropylene glycol is added in any stage of the process. Preferably, it represents up to 45%, more preferably from 3% to 45%, even more preferably from 10% to 40% by weight of the total weight of the perfuming composition.

The weight ratio between tricyclodecanedimethanol alcohol and dipropylene glycol in the perfuming composition is preferably from 3:1 to 1:1.

It has been found that the combination of a high heating phase of tricyclodecanedimethanol alcohol and a specific weight ratio between tricyclodecanedimethanol alcohol and dipropylene glycol could retard and/or prevent significantly the recrystallization of tricyclodecanedimethanol alcohol when incorporated in a perfuming composition.

Therefore, according to a particular embodiment, the weight ratio between tricyclodecanedimethanol alcohol and dipropylene glycol is 5:3.

According to another embodiment, the perfumery carrier further comprises one co-solvent chosen in the group consisting of hexylene glycol (2-methylpentane-2,4-diol), glycerol, 1,2-pentanediol, 1,2-hexanediol, D,L-1,2-isopropylidene glycerol, propanediol, butanediol and mixtures thereof.

Co-solvents can be added in step (i) and/or step (ii) and/or step (iii) according to their boiling point and the heating temperature set in each step.

According to a particular embodiment, the co-solvent is hexylene glycol.

According to an embodiment, co-solvent(s) is (are) used in an amount between 0 and 30%, preferably between 5 and 30% by weight based on the total weight of the composition.

Optional Aqueous Phase

According to a particular embodiment, an aqueous phase preferably in an amount comprised between 0.01 and 1% by weight based on the total weight of the composition is added in step (ii) or in step (iii) of the process.

Optional Ingredients

Perfumery adjuvant ingredients may be added in the process of the invention, preferably in step (iii), or directly into the perfume oil that is added in step (ii) or in step (iii).

By "perfumery adjuvant" we mean here an ingredient capable of imparting added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

As non-limiting examples, one may cite coloring agents, preservatives, pH adjusters, antioxidants, chelating agents, UV filters, quenchers, silicon oils, and mixture thereof.

Such optional perfumery adjuvant will represent no more than 5% w/w, or even 2% w/w, the percentages being relative to the total weight of the composition.

Another object of the invention is a perfuming composition obtainable by the process as defined above.

Another object of the invention is a consumer product, preferably in the form of a fine fragrance product or an air freshener product comprising the perfuming composition as defined above.

Fine fragrance products are preferably in the form of a perfume concentrates, perfumes, extract, mukhallat, attar.

The invention will now be further described by way of examples. It will be appreciated that the invention as claimed is not intended to be limited in any way by these examples.

EXAMPLES

Sample preparation: TCD alcohol DM is heated at 60° C. (comparative composition) or at 120° C. (compositions according to the invention) during 1 hour, then it is cooled down to 60° C. before adding dipropylene glycol and the perfuming oil.

Stability performance: In all examples below, stability to crystallization was visually assessed as a function of time. The beginning of crystallization generally results in a cloudy aspect of the sample and evolves towards a strong precipitation and deposition of small crystals at the bottom of the sample.

Perfume oil: The following perfume oil was used in the example (see table 1-a)

TABLE 1-a

Composition of fragrance F1

| Ingredient | Parts |
|---|---|
| 10-UNDECENAL | 2 |
| AMBROX ®[1)] | 260 |
| ASTROTONE | 2570 |
| BENZYL ACETATE | 20 |

TABLE 1-a-continued

Composition of fragrance F1

| Ingredient | Parts |
|---|---|
| BENZYL ALCOHOL | 6 |
| BENZYL SALICYLATE | 110 |
| CITRONELLOL | 1 |
| CITRONELLYL ACETATE | 8 |
| COUMARIN | 7 |
| DIPROPYLENGLYCOL | 5670 |
| 4-(1,1-DIMÉTHYLÉTHYL)-1-CYCLOHEXYLE ACETATE | 260 |
| ETHYLVANILLINE | 4 |
| GERANIOL | 6 |
| GERANYL ACETATE | 1 |
| HELIOTROPIN | 2 |
| HEXYLCINNAMIC ALDEHYDE | 40 |
| HYDROXYCITRONELLAL | 6 |
| ISOEUGENYL ACETATE | 2 |
| LILIAL | 20 |
| LINALYL ACETATE | 10 |
| LYRAL | 1 |
| METHYLIONONE ALPHA ISO | 30 |
| PHENOXYETHYL ISOBUTYRATE | 3 |
| PHENYLETHYL ACETATE | 2 |
| PHENYLETHYL ALCOHOL | 40 |
| ROSINOL[2] | 100 |
| SANDELA ® | 9 |
| STYRALLYL ACETATE | 8 |
| TONALIDE[3] | 560 |
| UNDECALACTONE GAMMA | 2 |
| (2,2-DIMETHOXYETHYL)BENZENE | 1 |
| Total parts | 9758 |

[1])(−)-(8R)-8,12-epoxy-13,14,15,16-tetranorlabdane, Firmenich SA, Geneva, Switzerland
[2])(+−)-2,2,2-trichloro-1-phenylethyl acetate
[3])1-(3,5,5,6,8,8-hexamethyl-5,6,7,8-tetrahydro-2-naphthalenyl)ethanone Example 1

Preparation of Perfuming Compositions and Evaluation of the Stability Performance

TABLE 2

Compositions comprising perfume, TCD alcohol DM (heated at different temperatures), and dipropylene glycol (DiPG)

| | Comparative composition X % wt | Composition A % wt | Composition B % wt |
|---|---|---|---|
| tricyclodecanedimethanol alcohol[1] | 60 | 60 | 50 |
| DiPG[2] | 20 | 20 | 30 |
| Fragrance F1[3] | 20 | 20 | 20 |
| Heating temperature for TCD alcohol DM | 60° C. | 120° C. | 120° C. |

[1])TCD alcohol DM, Origin: Oxea
[2])Origin: Firmenich SA, Geneva, Switzerland
[3])See table 1-a All the compositions listed in Table 2 were visually assessed transparent clear before letting the samples at room temperature and observe their evolution upon time.

The comparative composition X shows recrystallization after 14 days stability tests.

By contrast, composition A prepared according to the process of the invention exhibits also some recrystallization but only after 6 months storage at room temperature.

Furthermore, combining a high heating phase for TCD alcohol DM with a specific ratio between TCD alcohol DM and DIPG (50:30) extend the physical stability of the mixture since composition B prepared according to the process of the invention is still transparent without any recrystallization after 6 months at room temperature.

The invention claimed is:

1. A process for preparing a perfuming composition comprising the steps of:
 (i) Heating a viscosifying agent comprising tricyclodecanedimethanol alcohol at a temperature greater than 90° C.,
 (ii) Optionally, cooling down the solution obtained in step (i) at a temperature greater than room temperature, and
 (iii) Cooling down the mixture obtained in step (i) or (ii) to room temperature,
 wherein a perfumery carrier comprising dipropylene glycol is further added at any stage of the process, and
 wherein a perfume oil comprising at least one perfuming ingredient is further added in step (ii) and/or in step (iii).

2. The process according to claim 1, wherein at least 5% by weight of tricyclodecanedimethanol alcohol based on the total weight of the perfuming composition is added in step (i).

3. The process according to claim 1, wherein up to 50% by weight of the perfume oil based on the total weight of the perfuming composition is added in step (ii) or in step (iii).

4. The process according to claim 1, wherein up to 45% by weight of dipropylene glycol based on the total weight of the perfuming composition is added at any stage of the process.

5. The process according to claim 1, wherein the weight ratio between tricyclodecanedimethanol alcohol and dipropylene glycol in the perfuming composition is from 3:1 to 1:1.

6. The process according to claim 5, wherein the weight ratio between tricyclodecanedimethanol alcohol and dipropylene glycol is 5:3.

7. The process according to claim 1, wherein the perfumery carrier further comprises at least one co-solvent chosen from the group consisting of hexylene glycol, glycerol, 1,2-pentanediol, 1,2-hexanediol, D,L-1,2-isopropylidene glycerol, propanediol, butanediol and mixtures thereof at any stage of the process.

8. The process according to claim 7, wherein the co-solvent is added in an amount between 5 and 30% by weight based on the total weight of the composition.

9. The process according to claim 1, wherein an aqueous phase is added in step (ii) or in step (iii).

10. A perfuming composition obtainable by the process as defined in claim 1.

11. A consumer product comprising the perfuming composition as defined in claim 10.

12. The process according to claim 1, wherein cooling down the solution obtained in step (i) occurs at a temperature between 30° C. and 80° C.

13. The process according to claim 1, wherein an aqueous phase is added in step (ii) or in step (iii) in an amount between 0.01 and 1% by weight based on the total weight of the composition.

14. The consumer product according to claim 11, wherein the consumer product is in the form of a fine fragrance product or an air freshener.

* * * * *